(12) United States Patent
Arseneau

(10) Patent No.: US 8,754,376 B2
(45) Date of Patent: Jun. 17, 2014

(54) SYSTEMS AND METHODS FOR DETERMINING A ZERO BASELINE VALUE OF A CHANNEL FROM A DETECTOR DEVICE

(75) Inventor: Roger E. Arseneau, Buffalo Grove, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 861 days.

(21) Appl. No.: 12/962,093

(22) Filed: Dec. 7, 2010

(65) Prior Publication Data

US 2012/0143036 A1 Jun. 7, 2012

(51) Int. Cl.
*G01T 1/20* (2006.01)
*H01L 27/146* (2006.01)
*G01J 1/42* (2006.01)

(52) U.S. Cl.
USPC ............... 250/369; 250/395; 250/370.09

(58) Field of Classification Search
USPC .................... 250/369, 395, 370.09
See application file for complete search history.

(56) References Cited

U.S. PATENT DOCUMENTS

| 5,689,115 A * | 11/1997 | Balan et al. ............. 250/363.07 |
| 5,847,395 A | 12/1998 | Malmin et al. |
| 2004/0188623 A1 | 9/2004 | Breeding et al. |
| 2008/0298475 A1* | 12/2008 | Huang ..................... 375/257 |
| 2009/0185613 A1* | 7/2009 | Agazzi et al. ............. 375/232 |

* cited by examiner

*Primary Examiner* — David Porta
*Assistant Examiner* — Mindy Vu
(74) *Attorney, Agent, or Firm* — Peter Kendall

(57) ABSTRACT

A representative method for determining a zero baseline value of a channel from a detector device of a nuclear medicine imagining system to allow for correction caused by noise or interference on the detector device includes calculating a first value of a baseline based on a first sample of analog electrical signals from analog-to-digital converters (ADCs) coupled to the detector device; comparing a predetermined value with the first value of the baseline; determining whether there is a small change between the predetermined value and the first value of the baseline; and responsive to determining that the small change exists, adjusting the baseline of the ADCs by a fraction of the small change based on the comparison between the predetermined value and the first value of the baseline.

15 Claims, 7 Drawing Sheets

SYSTEMS AND METHODS FOR DETERMINING A ZERO BASELINE VALUE OF A CHANNEL FROM A DETECTOR DEVICE

TECHNICAL FIELD

The present disclosure is generally related to nuclear medicine imaging for obtaining images of a patient's body organs of interest. In particular, the present disclosure relates to methods and systems for determining the integrated value of scintillation events in positron emission tomography (PET) and single photon emission computed tomography (SPECT) nuclear medicine imaging systems.

BACKGROUND

Nuclear medicine imaging is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body. One or more detectors are used to detect the emitted gamma photons, and the information collected from the detector(s) is processed to calculate the position of origin of the emitted photon from the source (e.g., the body organ or tissue under study). The accumulation of a large number of emitted gamma positions allows an image of the organ or tissue under study to be displayed.

For example, in PET and SPECT nuclear medicine imaging systems, emitted gamma photons are typically detected by placing a scintillator over the region of interest. Such scintillators are conventionally made of crystalline material such as thallium activated sodium iodide, NaI(Tl) or leutetium oxyorthosilicate (LSO), which interacts with absorbed gamma photons to produce flashes of visible light. The light photons emitted from the scintillator crystal are in turn detected by photo sensor devices that are optically coupled to the scintillator crystal, such as photomultiplier tubes or avalanche photodiodes (APD). The photo sensor devices convert the received light photons into electrical pulses whose magnitude corresponds to the amount of light photons impinging on the photosensitive area of the photo sensor device.

Not all gamma interactions in a scintillator crystal can be used to construct an image of the target object. Some of the interactions may be caused by gamma photons that were scattered or changed in direction of travel from their original trajectory. Thus, one conventional method that has been used to test the validity of a scintillation event is to compare the total energy of the scintillation event against an energy "window" or range of expected energies for valid (e.g., unscattered) events. In order to obtain the total energy of the event, light pulse detection voltage signals generated from each photo sensor device as a result of a single gamma interaction are typically integrated from the start of each pulse, and then added together to form an energy signal associated with a particular event. Energy signals falling within the predetermined energy window are considered to correspond to valid events, while energy signals falling outside of the energy window are considered to correspond to scattered, or invalid, events, and the associated event is consequently not used in the construction of the radiation image, but is discarded. To get an accurate measure of the event from an output of an analog-to-digital converter (ADC), the value of the ADC zero (baseline) is typically subtracted from each sample used to form the integration sum of the scintillations. The baseline value in both PET and SPECT systems can be affected by DC offsets in the ADC and amplifiers, shifts to the AC coupling as a function of count rate, noise from the detection photo sensor and large noise voltages induced by a gradient coil in a magnetic resonance imaging (MRI) system.

Desirable in the art is an improved nuclear medicine imaging system that would determine a more accurate integrated value of scintillation events in PET and SPECT nuclear medicine imaging systems.

SUMMARY

A representative method for determining a zero baseline value of a channel from a detector device of a nuclear medicine imagining system to allow for correction caused by noise or interference on the detector device includes calculating a first value of a baseline based on a first sample of analog electrical signals from ADCs coupled to the detector device; comparing a predetermined value with the first value of the baseline; determining whether there is a small change between the predetermined value and the first value of the baseline; and responsive to determining that the small change exists, adjusting the baseline of the ADCs by a fraction of the small change based on the comparison between the predetermined value and the first value of the baseline.

According to another aspect of the present disclosure, a nuclear medicine imaging system is disclosed. The system comprises one or more detectors that receive gamma photons; one or more ADCs that are coupled to the one or more detectors, wherein the one or more ADCs receive analog electrical signals from the one or more detectors corresponding to the received gamma photons and convert the analog electrical signals to digital signals by taking samples of the analog electrical signals; one or more baseline calculation devices for receiving the samples of the analog electrical signals from the respective one or more ADCs, wherein the one or more baseline calculation devices track a baseline of the digital signals from the respective ADCs for slow changes in the baseline. When the one or more baseline calculation devices track slow changes in the baseline, the one or more baseline calculation devices perform the following: calculating a first value of the baseline based on a first sample of the analog electrical signals from the respective ADCs; comparing a predetermined value with the first value of the baseline; determining whether there is a small change between the predetermined value and the first value of the baseline. When there is a small change between the predetermined value and the first value of the baseline, the one or more baseline calculation devices adjust the baseline of the digital signals by a fraction of the small change based on the comparison between the predetermined value and the first value of the baseline. The system further comprises a processing device for receiving and processing the digital signals based on the adjusted baseline to facilitate generating an image data.

Other systems, devices, methods, features of the present disclosure will be or will become apparent to one skilled in the art upon examination of the following figures and detailed description. It is intended that all such systems, devices, methods, features be included within the scope of the present disclosure, and be protected by the accompanying claims.

BRIEF DESCRIPTION OF DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, the reference numerals designate corresponding parts throughout the several views. While several embodiments are described in connection with these drawings, there is no intent to limit the disclosure to the embodiment or embodiments disclosed herein. The intent is to cover all alternatives, modifications, and equivalents.

DETAILED DESCRIPTION

Examples of nuclear medicine imaging systems according to the present disclosure are first discussed with reference to the figures. Although these systems are described in detail, they are provided for purposes of illustration only and various modifications are feasible. After the examples of the nuclear medicine imaging systems are described, examples of flow diagrams of the systems are provided to explain the manner in which a zero baseline value of a channel from a detector device of a nuclear medicine imagining system can be determined.

Figure 1:
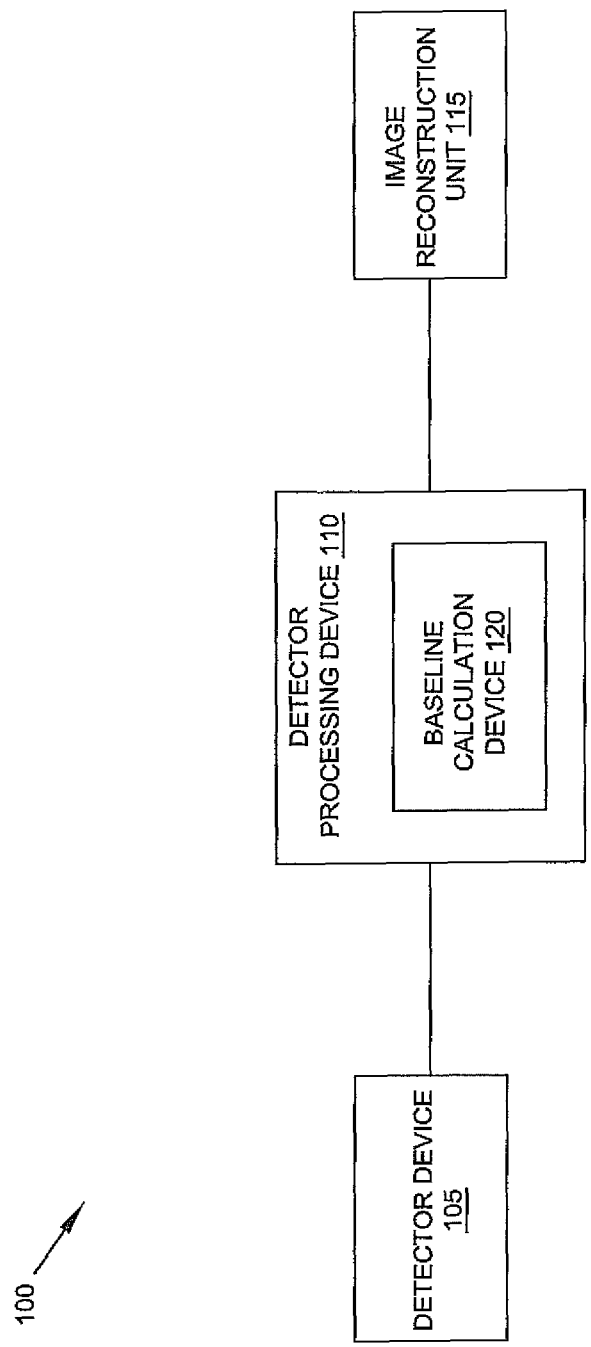
FIG. 1 is a high-level block diagram of a nuclear medical imaging system having a baseline calculation device in accordance with an embodiment of the present disclosure.

FIG. 1 is a high-level block diagram of a nuclear medicine imaging system 100 having a baseline calculation device 120 in accordance with an embodiment of the present disclosure. The nuclear medicine imaging system 100 can include, but is not limited to, a PET, a SPECT system and a positron emission tomography—MR dual modality system. The nuclear medicine imaging system 100 includes a detector device 105 that detects gamma photons from a target and converts gamma photons to analog electrical signals. The detector device 105 sends the analog electrical signals associated with the detected gamma photons to a detector processing device 110 for pre-processing of the electrical signals, including the calculation of baseline values of the electrical signals. The detector processing device 110 puts the electrical signals in condition for an image reconstruction unit 115 to reconstruct the processed electrical signals into an image data that is generated using mathematical image reconstruction procedures.

Figure 2:
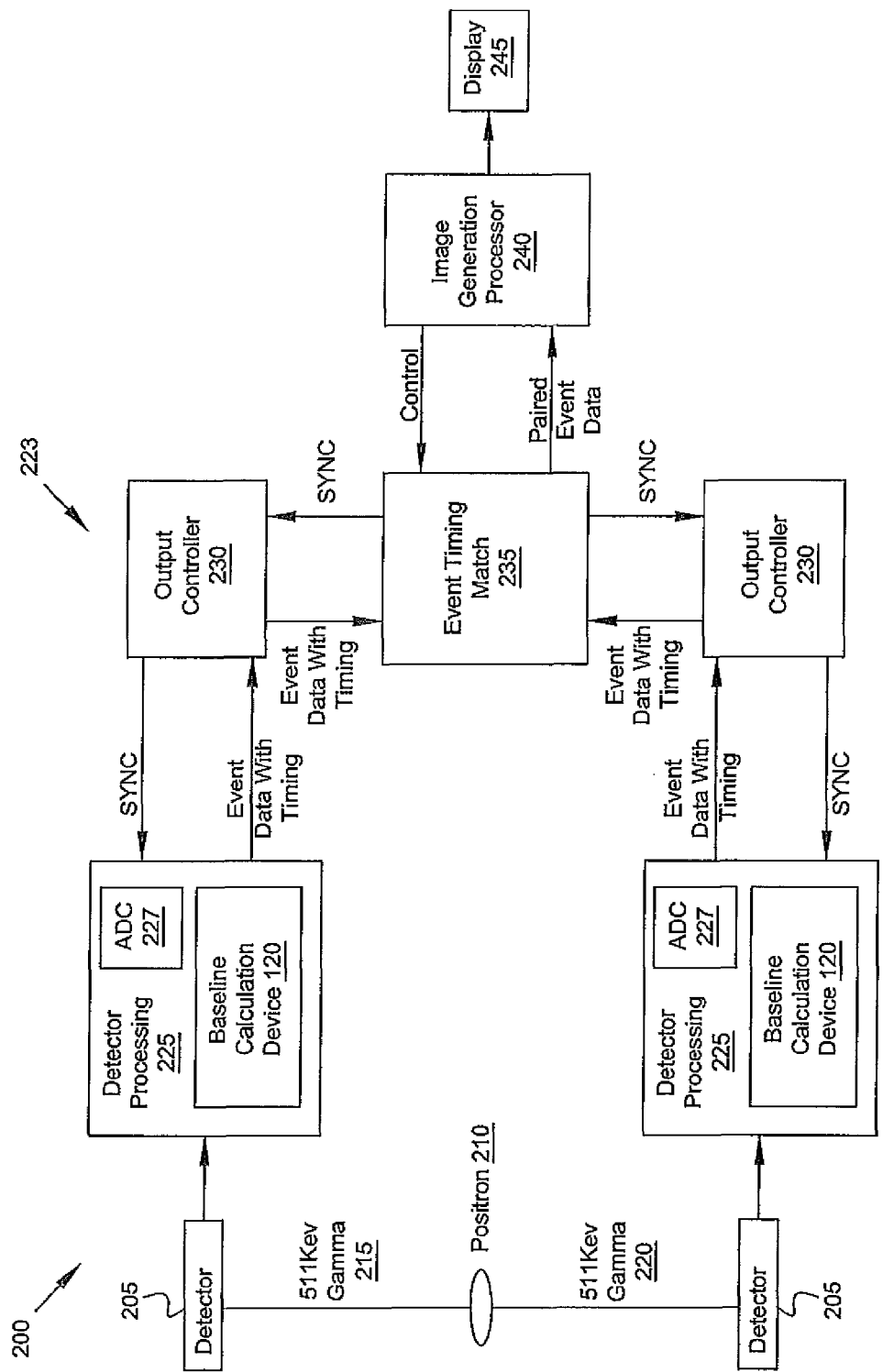
FIG. 2 is a high-level block diagram of a PET system having a baseline calculation device in accordance with an embodiment of the present disclosure.

FIG. 2 is a high-level block diagram of a PET system 200 having a baseline calculation device 120 in accordance with an embodiment of the present disclosure. The PET detector device 205 can include scintillator crystals (not shown) and photomultipliers (not shown). In general, a living subject is injected with a short-lived radioactive tracer isotope (e.g., usually into blood circulation) before conducting a positron emission tomography scan. The tracer isotope is, for example, fluorodeoxyglucose (FDG), which is a type of sugar. During the PET scan, data is recorded from the tracer-concentrated tissue as the tracer isotope decays.

As the tracer-concentrated tissue undergoes positron emission decay, the tissue emits a positron 210, which is an antiparticle of the electron with opposite charge. The positron 210 eventually collides with an electron, producing a pair of annihilation (gamma) photons 215, 220 (e.g., 511 keV gamma) moving in opposite directions. The gamma photons 215, 220 are detected when they reach the scintillator crystals at the detector 205, creating a burst of light which is detected and converted to analog electrical signals by the photomultipliers.

The pair of photons moves in approximately opposite direction and are processed whether the detected pair of photons are a coincidence event by a coincidence processing unit 223. To process this, the electrical signals from the photomultipliers is sent to detector processing devices 225, which each includes, but is not limited to, analog-to-digital converters 227 and a baseline calculation device 120. The analog-to-digital converters 227 convert to the analog electrical signals from the photomultipliers to digital signals, which are sent to a baseline calculation device 120 to calculate the baseline value of the digital signals. The baseline calculation device 120 is further described in connection with FIGS. 5-7. The detector processing devices 225 process an event data with timing based on the calculated baseline value of the digital signals.

Output controllers 230 receive the event data with timing from and send a sync data to the respective detector processing devices 225. An event timing match device 235 receives the event data with timing from and sends a sync data to the respective output controllers 230. If the event data with timing (that are associated with the detected pair of photons) are determined to be a coincidence event, the event timing match device 235 sends the paired event data to an image generation processor 240 for an image data that is generated using mathematical image reconstruction procedures. A display device 245 displays the image data.

Figure 3:
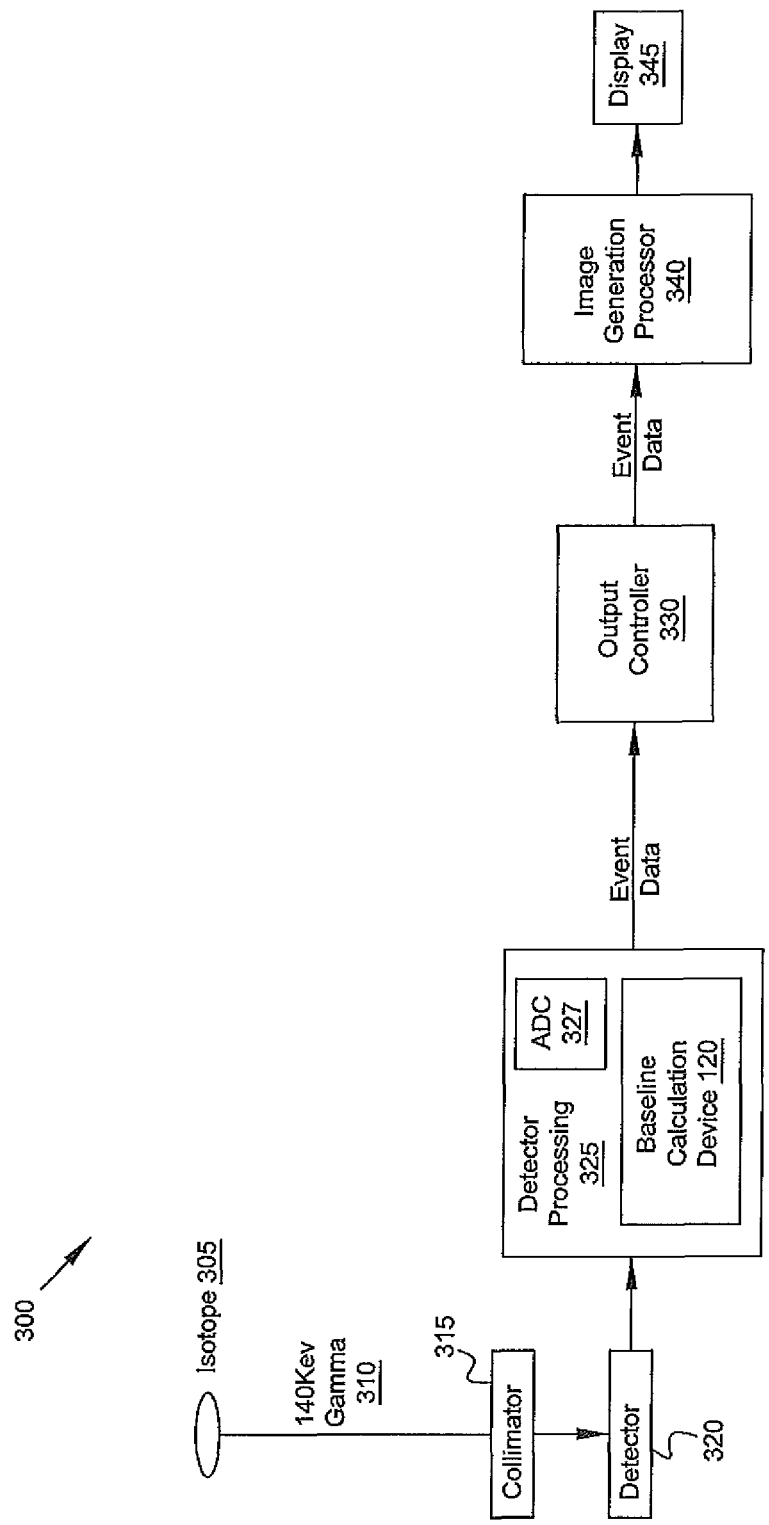
FIG. 3 is a high-level block diagram of a SPECT system having a baseline calculation device in accordance with an embodiment of the present disclosure.

FIG. 3 is a high-level block diagram of a SPECT system 300 having a baseline calculation device 120 in accordance with an embodiment of the present disclosure. In this example, the architecture of the SPECT system 300 is similar to the architecture of the PET system 200 as described in FIG. 2. The SPECT system 300 includes a baseline calculation device 120, detector processing device 325, analog-to-digital converters 327, output controller 330, image generation processor 340, and a display device 345, all of which function similarly to the components as in the PET system 200 (FIG. 2), However, the SPECT radioactive substance is a gamma-emitting radioisotope 305 and has a longer decay time than the PET radioactive tracer isotope. The SPECT gamma-emitting radioisotope 305 emits a single gamma ray instead of double gamma rays as in the PET system 200.

The process of obtaining 3D information using the SPECT system 300 begins with an injection of a gamma-emitting radioisotope 305 into the bloodstream of a patient. Often, a marker radioisotope 305 is combined with a special radioligand because the radioligand has chemical binding properties that enables the radioisotope 305 to bind to certain types of tissues. Once the radioisotope reaches a desirable location in the body of the patient, the gamma-emission of the isotope allows the ligand concentration to be seen by a gamma detector device 320.

For example, the isotope 305 collides with an electron, producing an annihilation (gamma) photons 310 (e.g., 140 keV gamma). The gamma photons 310 are detected by a detector 320 when they reach the detector 320 after being collimated by a collimator 315, which directs the photons in a specific direction towards a detector 320. The detector 320 converts the photons to analog electrical signals. The remaining components, as mentioned above, function similarly to the components as in the PET system 200 (FIG. 2).

Figure 4:
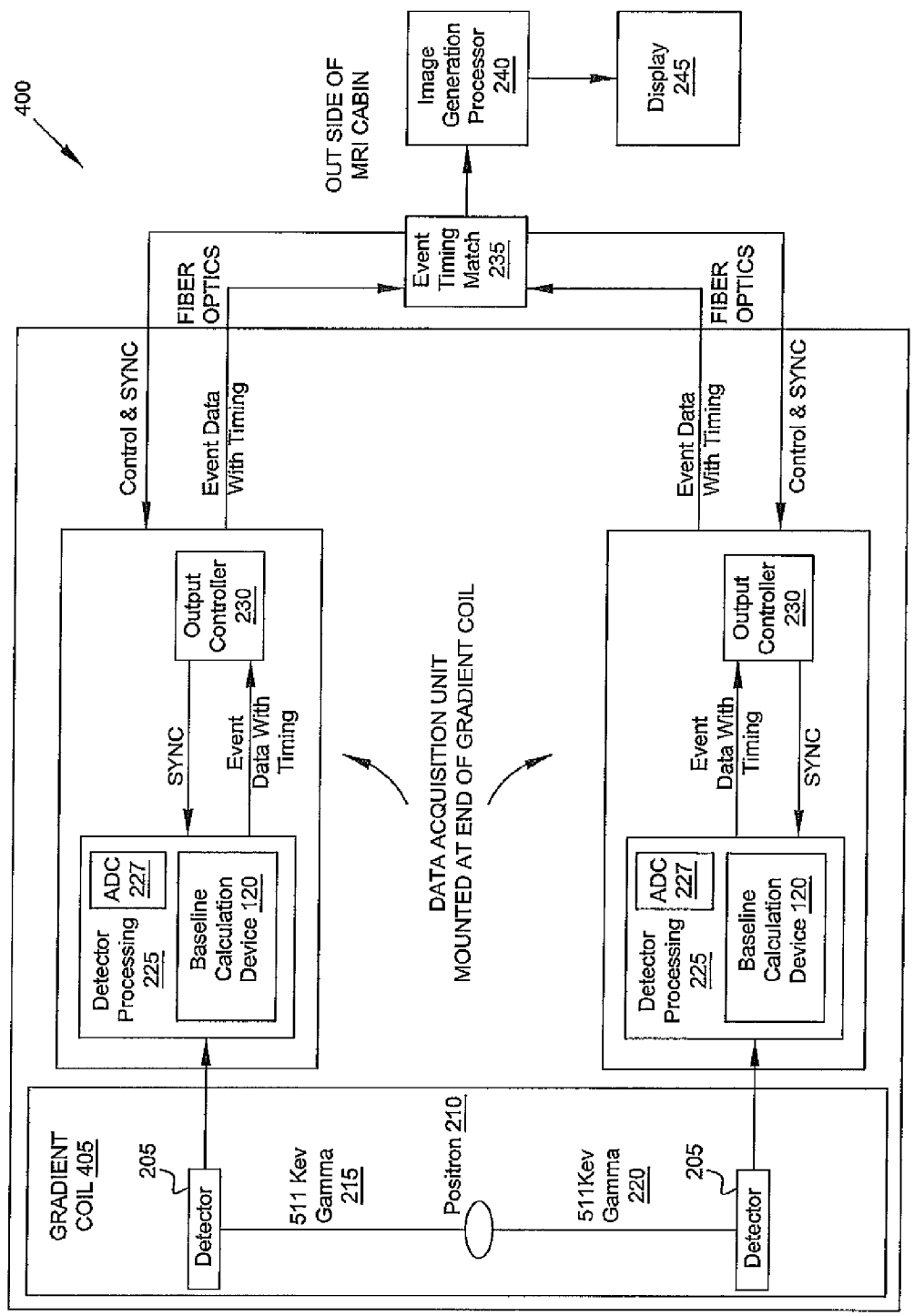
FIG. 4 is a high-level block diagram of a PET—magnetic resonance (MR) dual modality system having a baseline calculation device in accordance with an embodiment of the present disclosure.

FIG. 4 is a high-level block diagram of a PET—MR dual modality system 400 having a baseline calculation device 120 in accordance with an embodiment of the present disclosure. In this example, the architecture of the PET-MR system 400 is similar to the architecture of the PET system 200 as described in FIG. 2, which includes PET detector devices 205, baseline calculation device 120, detector processing device 225, analog-to-digital converters 227, output controller 230, event timing match 235, image generation processor 240, and display device 245, all of which function similarly to the components as in the PET system 200. However, the MR-PET dual modality system 400 includes MR coils 405 inserted within a ring of the PET detector devices 205. Because of the magnetic fields generated by the MR gradient coil 405, there are noises induced into the PET electronics that the PET system 200 does not have to deal with. The design of the baseline calculation device 120 can calculate an accurate baseline value of the digital signals despite the interference generated by the MR gradient coils 405. The baseline calculation device 120 is described in further detail in connection with FIGS. 5-6.

Figure 5:
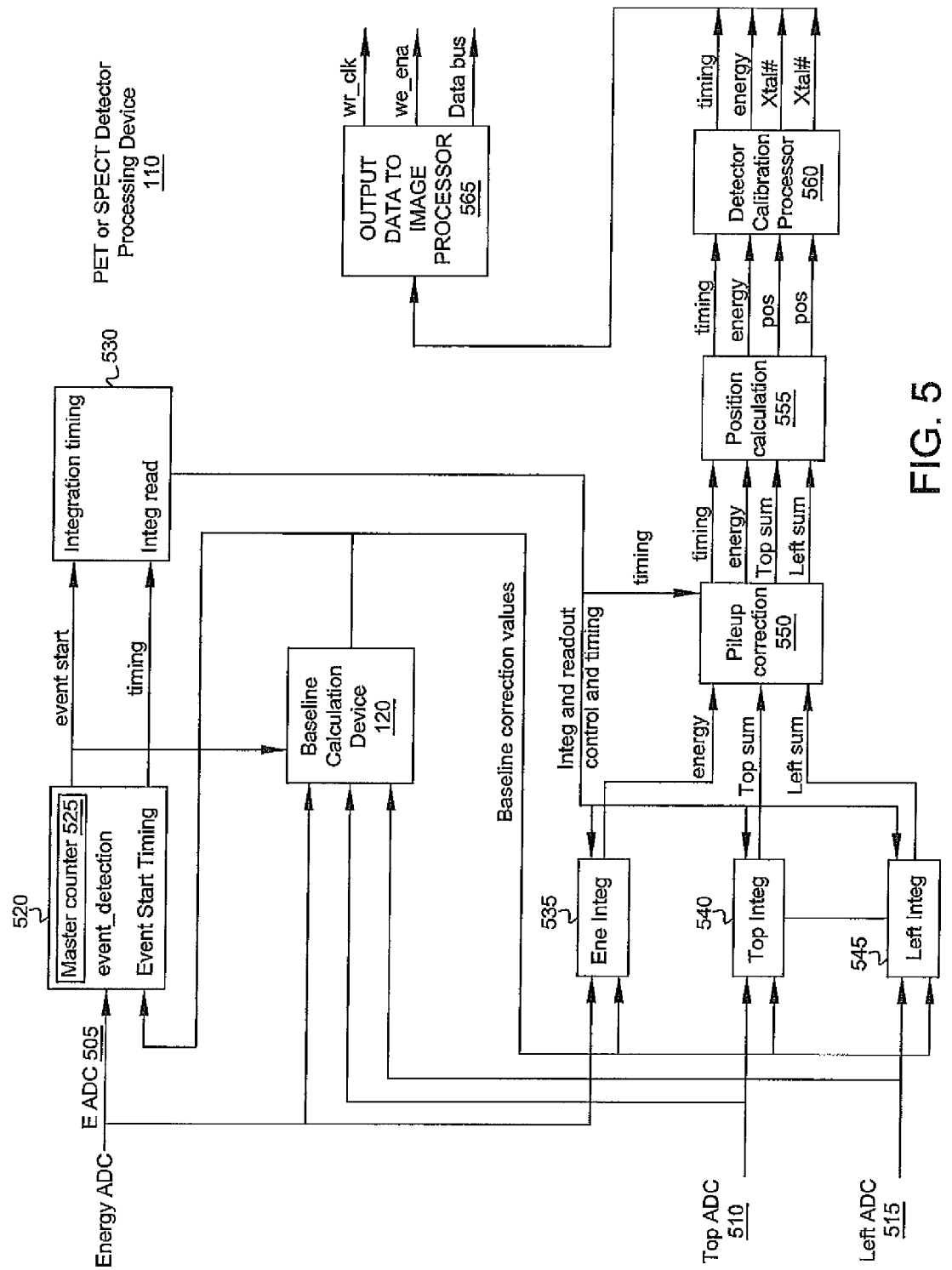
FIG. 5 is a detailed block diagram of a detector processing device, such as that shown in FIG. 1.

FIG. 5 is a detailed block diagram of an example of a detector processing device 110, such as that shown in FIG. 1. The detector device 105 can output three signals associated with energy, top and left channels, which are passed through low pass analog filters (not shown) and then digitized into energy signals 505, top signals 510, and left signals 515 by the ADCs 227, 327 (see FIGS. 2-3). The ADCs convert the analog electrical signals to digital signals by taking samples of the analog electrical signals.

The digitized signals 505, 510, 515 are processed by the baseline calculation device 120 to determine an accurate zero baseline value of each channel to allow correction of noise or interference on the detector device 105, such as changes due to count rate and gradient coil induced baseline shifts. The determined zero baseline values can be used to correct the integrated value of the energy, top and left channels. The energy baseline value can also be used to correct the event detection and timing functions. The functions of the baseline calculation device 120 are further described in connection with FIGS. 6-7.

A brief description of the remaining components in FIG. 5 is provided hereinafter for a better understanding and appreciation of the nuclear medicine imaging system already described above. An event detection device 520 detects when there is an event present in the energy ADC output signal 505 and calculates the start time of the event relative to a master clock counter 525. Such counter 525 passes the timing and event start information to an integration control device 530. The event detection device 520 can re-sample the energy digital signals at, for example, 40 MHz and delay the energy waveform to align with the top and left waveforms for energy, top, and left integrators 535, 540 and 545, respectively, to operate on the same or substantially the same number of samples and phase relationship.

The integration control device 530 starts and stops the energy, top, and left integrators 535, 540, 545 to take into account the delay between event detection and when the event is in the top and left ADC output signals 510, 515. The integration detection device 530 also processes bad event dumping and pileup timing of the energy, top, and left integrators 535, 540, 545.

The top, left and the re-sampled energy signals are digitally integrated to get the total sum output from each input. The energy, top, and left integrators 535, 540, 545 sum the waveform samples when instructed by the integration control form device 530. The energy, top, and left integrators 535, 540, 545 also sum the determined baseline values and subtracts them from the integrated total sum output before passing them on. If before the integration is complete a second event occurs, the first integration is stopped before any of the second event can become part of the integrated sum output and a second integration is started.

A pileup correction device 550 receives and corrects the event integrated values for pileup and then passed on to a position calculation device 555. Such position calculation device 555 takes the corrected top and left integrated sums and divides them by the corrected integrated energy sum to get the position in two dimensions:

Top/Energy=$X$ position

Left/Energy=$Y$ position

A detector calibration processor 560 uses the X and Y position values to determine the crystal number in which the scintillation occurred. The crystal number is used to adjust the energy value and select the energy window for the given crystal and use that to qualify the event to be passed to the output multiplexer. The crystal number is also used to correct the timing data generated by the event detection device 520. If the corrected time indicates the event occurred in an earlier or later sync period the event can be moved one sync period forward or backward as appropriate. An output device 565 receives the data from the detector calibration processor 560 and sends it to the image reconstruction unit 115.

Figure 6:
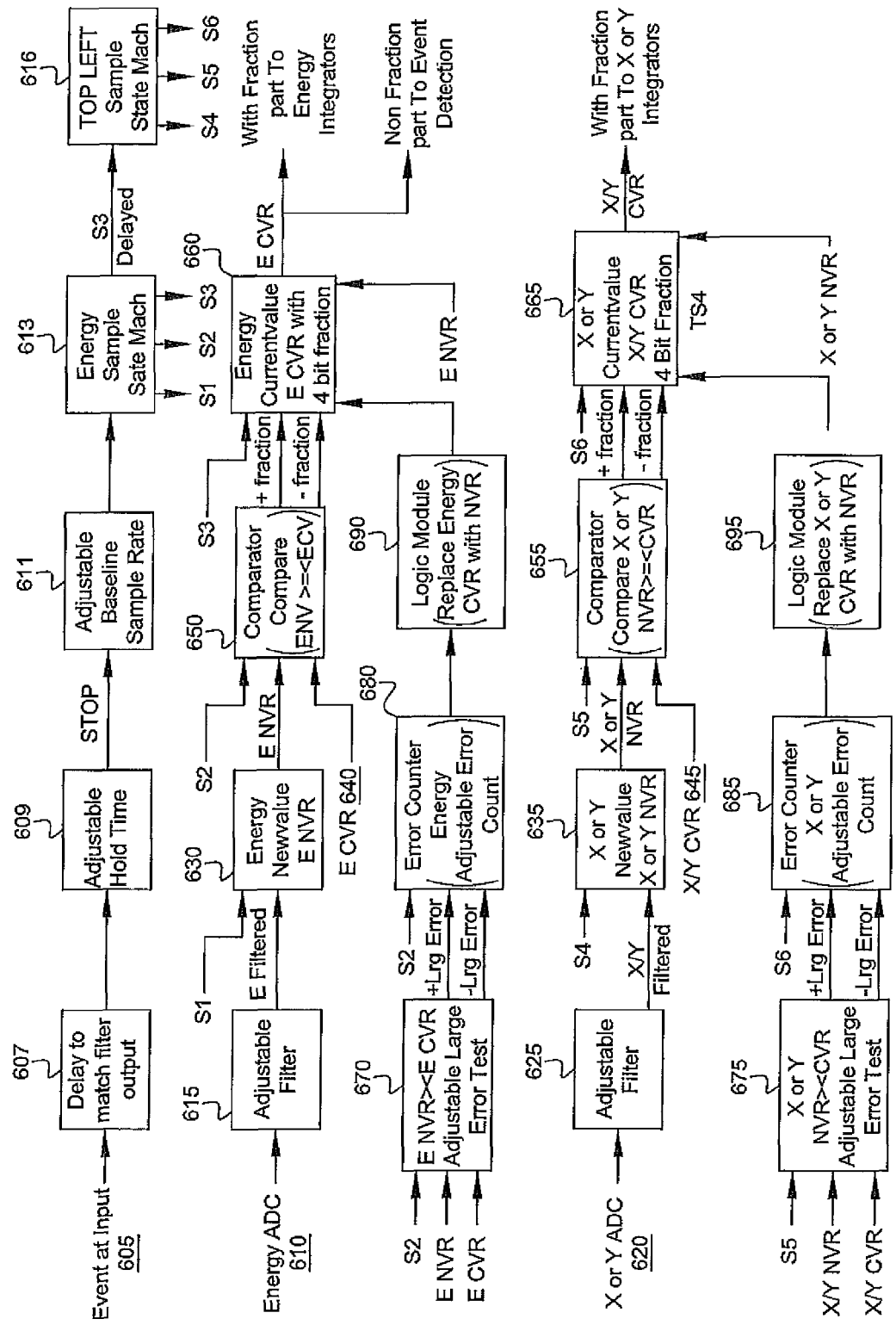
FIG. 6 is a block diagram that illustrates an embodiment of a baseline calculation device in accordance with an embodiment of the present disclosure.

FIG. 6 is a block diagram that illustrates an embodiment of a baseline calculation device 120 in accordance with an embodiment of the present disclosure. The baseline calculation device 120 receives a detected event signal 605 at input to determine when an event is present to prevent the baseline from sampling during an event. If the event signal 605 is detected, the event signal 605 is delayed by the logic module 607 to match the filter output and can be adjustably held 609 for a period of time. The baseline calculation device 120 can adjust the baseline sample rate 611 to the event signal 605 and generate energy sample 613 and top left sample 616 using state machines S1, S2, S3, S4, S5, S6.

The output signal 610 from the energy ADC is filtered by an adjustable filter 615 with, for example, a 32 point smoothing that reduces the average peak to peak noise. The output signal 620 of the X and Y ADC is filtered by an adjustable filter 625 with, for example, a 4 point smoothing that reduces the peak to peak noise.

The baseline calculation device 120 uses two methods to track the baseline. The first method is for tracking slow changes in the baseline and the second is for tracking fast changes caused by, for example, the gradient coil 405 (FIG. 4).

The slow method works as follows. The smoothed value of the energy, top and left ADCs are sampled at a predetermined rate as long as there is not an event at the input of the detector. A register for each channel is loaded with the smooth value at the time of sample and is called the NEWVALUE (NVR) 630, 635 for each channel. There is a second register for each channel called the CURRENTVALUE (CVR) 640, 645 which has, for example, 4 more bits then the NVR whose 4 lower bits represent a fraction (e.g., ⅟₁₆) of a least significant bit (LSB) of the smoothed data. Comparators 650, 655 compare the NVR 630, 635 with the upper bits (non-fraction bits) of the CVR 640, 645. If the CVR 640, 645 is greater than the NVR 630, 635, then a fraction is subtracted from the CVR 640, 645. If the CVR 640, 645 is less than the NVR 630, 635 then a fraction is added to the CVR 640, 645. If CVR 640, 645 is equal to the NVR 630, 635 there is no change. The non-fractional bits 660, 665 of the CVR 640, 645 are used as the baseline to correct the ADC outputs. The LSB of the non-fractional bits of the CVR has a weighting of one-quarter (¼) of an ADC LSB. This allows the CVR value 640, 645 to follow the average of the baseline for slow rates of change of up to about 3 ADC LSB per micro second.

The second method can allow the average value to change to the new value after a period of time (e.g., 81 nanoseconds) and/or after a predetermined number of times that a large change in the baseline has been detected. The period of time and the predetermined number of times can be any arbitrary number. Generally, the large change in the baseline is caused by the gradient coil 405. In one example, on every sample, the logic modules 670 and 675 tests the absolute value of the difference between the new value and the average against a set error value and if the absolute value is larger than the set error value, a memory is set. There are two memories, one for when the absolute value is greater than the set error value and a second one for when the absolute value is less than the set error value.

Error counters 680, 685 count the number of errors in the same direction. If the error is repeated in the same direction for a set number of times (e.g., 3, 4, 5 and 7 times), logic modules 690, 695 replace the average value by the new value of the last sample. If the error continues on the next sample the average value can continue to be replaced by the new value until the error is gone and the baseline tracking returns to the averaging method. The error value can be set to just above the average peak to peak noise and the number of error in a row can be set to, e.g., 5. This criterion that the error happens for a repeated number of times in the same direction keeps the averaging from being disturbed by larger noise pulses.

In a PET-MR detector using avalanche photodiodes (APD) to detect the gamma rays the output signal generally has a very high noise level. The baseline noise has a peak to peak value of, for example, 10 to 20 percent of the signal for a 511 key gamma ray 215, 220 (FIG. 2). This baseline shifts with the count rate because the detector has capacitor coupling due to the high gain of an amplifier to amplify the APD signals. The baseline value is used to process the detector output signals and needs to have a high accuracy of the 511 key gamma ray signal to produce good position and energy resolution. This is done by sampling the baseline at a high frequency and averaging the samples in an averaging circuit that has a low cut off frequency to produce a baseline value that follows the slow variation in the output baseline.

When the MRI gradient coil is driven and produces rapid changing magnetic fields that cause fast changes in the baseline that the low frequency baseline averaging cannot follow, the fast change method allows the baseline to get to a new value quickly and return to averaging at the new baseline value to properly process the ADC output.

In a SPECT gamma detector where each photomultiplier tube (PMT) and the energy sum has an ADC and is digitally integrated to generate the PMT and energy signals to be used in the energy and position calculations, the ADC zero generally remains constant to a fraction of an LSB to achieve stable linearity and uniformity. In the detector, the gamma event is integrated by summing a number of samples to determine the area under the pulse output of each PMT and the total summed energy signal. For example, if there are 27 samples and the ADC output has a ½ LSB zero error the sum has an error of 27*½ LSB or 13.5 LSB error. To correct this error, there is a second summer that integrates the baseline at the same time as the ADC. The CVR has a 5 bit fraction giving a baseline value to ⅟₃₂ of an ADC LSB to determine the ADC DC offset error. The CVR can determine that an error is ½ an LSB (e.g., the LSB error is ½*32 or 16). After 27 samples the acclimated error number is 27*16 or 432. The number is then divided by 32 which is equal to 13.5 and subtracted from the integrated PMT or energy sum. This gives an integrated sum that is corrected for DC zero offsets of a fraction of an ADC LSB.

Figure 7:
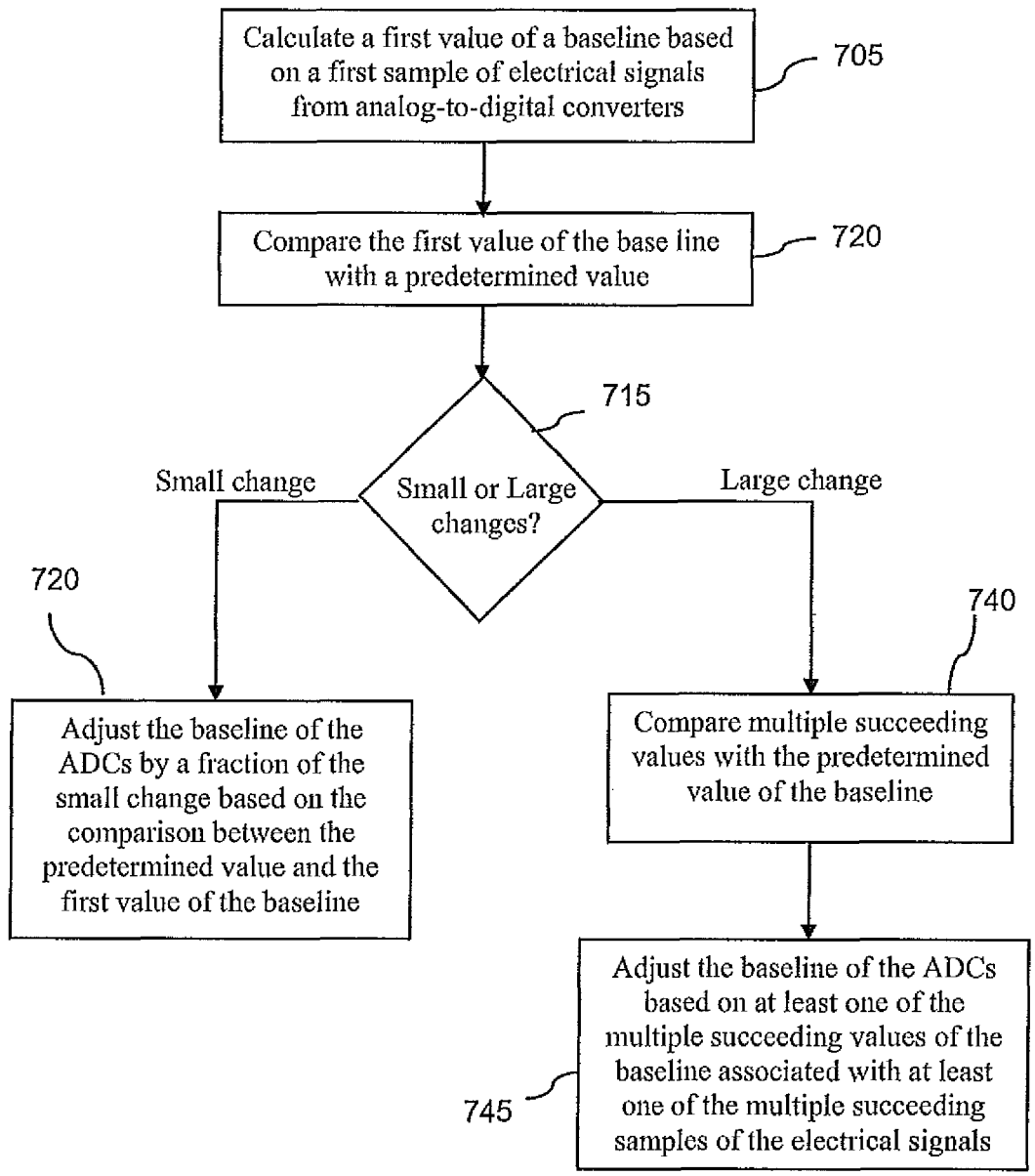
FIG. 7 is a flow diagram that illustrates an embodiment of the architecture, functionality, and/or operation of a baseline calculation device in accordance with an embodiment of the present disclosure.

FIG. 7 is a flow diagram that illustrates an embodiment of the architecture, functionality, and/or operation of a baseline calculation device in accordance with an embodiment of the present disclosure. The baseline calculation device 120 generally determines a zero baseline value of a channel from a detector device 105 (FIG. 1) of a nuclear medicine imagining system 100 (FIG. 1) to allow for correction caused by noise or interference on the detector device 105. Beginning with block 705, a first value of a baseline is calculated based on a first sample of analog electrical signals from analog-to-digital converters (ADCs) coupled to the detector device. In block 710, a predetermined value is compared with the first value of the baseline. In block 715, the baseline calculation device 120 determines whether there is a small change or a large change between the predetermined value and the first value of the baseline.

Responsive to determining that the small change exists, the baseline calculation device 120 in block 720 adjusts the baseline of the ADCs by a fraction of the small change based on the comparison between the predetermined value and the first value of the baseline. The determination of whether the small change exists is achieved by determining a difference between the predetermined value and the first value of the baseline, and responsive to determining that the difference is lesser than a first predetermined threshold, adjusting the baseline of the ADCs by the fraction of the difference.

Responsive to determining that a large change exists, the baseline calculation device 120 in block 725 compares multiple succeeding values with the predetermined value of the baseline. The multiple succeeding values are associated with multiple succeeding samples of the analog electrical signals from the respective ADCs. Responsive to determining that the large change exists between the multiple succeeding values and the predetermined value of the baseline, the baseline calculation device 120 in block 730 adjust the baseline of the ADCs based on at least one of the multiple succeeding values of the baseline associated with at least one of the multiple succeeding samples of the analog electrical signals.

The determination of whether the large change exists is achieved by determining whether there is a difference between the predetermined value and the first value of the baseline exceeds a second predetermined threshold; calculating multiple values of the baseline of the ADCs based on the multiple succeeding samples of the analog electrical signals from the respective ADC; calculating differences between the multiple values of the baseline and the predetermined value; and responsive to determining that the differences between the multiple values of the baseline and the predetermined value exceed a second predetermined threshold, adjusting the baseline based on at least one of the multiple values of the baseline from at least one of the multiple succeeding samples of the analog electrical signals.

Alternatively or additionally, the baseline calculation device 120 can adjust the baseline based on the differences between the multiple values of the baseline and the predetermined value exceeding the second predetermined threshold in the same direction for several succeeding samples of the analog electrical signals from the respective ADCs. Alternatively or additionally, the baseline calculation device 120 can adjust the baseline based on the differences between the multiple values of the baseline from multiple successive succeeding samples and the predetermined value exceeding the second predetermined threshold. Alternatively or additionally, the baseline calculation device 120 can adjust the baseline using the latest succeeding sample of the analog electrical signals from the respective ADCs.

It should be noted that any process descriptions or blocks in flowcharts should be understood as representing modules, segments, or portions of code which include one or more executable instructions for implementing specific logical functions or steps in the process. As would be understood by those of ordinary skill in the art of the software development, alternate embodiments are also included within the scope of the disclosure. In these alternate embodiments, functions may be executed out of order from that shown or discussed, including substantially concurrently or in reverse order, depending on the functionality involved.

The systems and methods disclosed herein can be implemented in software, hardware, or a combination thereof. In some embodiments, the system and/or method is implemented in software that is stored in a memory and that is executed by a suitable microprocessor (μP) situated in a computing device. However, the systems and methods can be embodied in any computer-readable medium for use by or in connection with an instruction execution system, apparatus, or device. Such instruction execution systems include any computer-based system, processor-containing system, or other system that can fetch and execute the instructions from the instruction execution system. In the context of this disclosure, a "computer-readable medium" can be any means that can contain, store, communicate, propagate, or transport the program for use by, or in connection with, the instruction execution system. The computer readable medium can be, for example, but not limited to, a system or propagation medium that is based on electronic, magnetic, optical, electromagnetic, infrared, or semiconductor technology.

Specific examples of a computer-readable medium using electronic technology would include (but are not limited to) the following: an electrical connection (electronic) having one or more wires; a random access memory (RAM); a read-only memory (ROM); an erasable programmable read-only memory (EPROM or Flash memory). A specific example using magnetic technology includes (but is not limited to) a portable computer diskette. Specific examples using optical technology include (but are not limited to) optical fiber and compact disc read-only memory (CD-ROM).

Note that the computer-readable medium could even be paper or another suitable medium on which the program is printed. Using such a medium, the program can be electronically captured (using, for instance, optical scanning of the paper or other medium), compiled, interpreted or otherwise processed in a suitable manner, and then stored in a computer memory. In addition, the scope of the certain embodiments of the present disclosure includes embodying the functionality of the preferred embodiments of the present disclosure in logic embodied in hardware or software-configured mediums.

This description has been presented for purposes of illustration and description. It is not intended to be exhaustive or to limit the disclosure to the precise forms disclosed. Obvious modifications or variations are possible in light of the above teachings. The embodiments discussed, however, were chosen to illustrate the principles of the disclosure, and its practical application. The disclosure is thus intended to enable one of ordinary skill in the art to use the disclosure, in various embodiments and with various modifications, as are suited to the particular use contemplated. All such modifications and variation are within the scope of this disclosure, as determined by the appended claims when interpreted in accordance with the breadth to which they are fairly and legally entitled.

What is claimed is:

1. A PET-MR dual modality nuclear medicine imaging system comprising:
   an MRI gradient coil;
   one or more detectors that receive gamma photons;
   one or more analog-to-digital converters (ADCs) that are coupled to the one or more detectors, wherein the one or more ADCs receive analog electrical signals from the one or more detectors corresponding to the received gamma photons and convert the analog electrical signals to digital signals by taking multiple succeeding samples of the analog electrical signals from the respective one or more ADCs;
   one or more baseline calculation devices for determining a zero baseline value of a channel from the one or more detectors to allow for correction of noise or interference on the detectors, the one or more baseline calculation devices configured for receiving the multiple succeeding samples of the analog electrical signals from the respective one or more ADCs, wherein the one or more baseline calculation devices track a baseline of the digital signals from the respective ADCs for slow changes in the baseline, wherein the slow changes mean a rate of change less than or equal to 3 ADC least significant bit per micro second, wherein the slow changes occur when the MRI gradient coil is not being driven, wherein the one or more baseline calculation devices perform the following for the slow changes in the baseline:
      calculating a first value of the baseline based on a first sample of the analog electrical signals from the respective ADCs;
      comparing a predetermined value with the first value of the baseline;
      determining a first difference between the predetermined value and the first value of the baseline; and
      responsive to determining that the first difference is less than a first predetermined threshold, adjusting the baseline of the digital signals by a fraction of the difference; and
   a processing device for receiving and processing the digital signals based on the adjusted baseline to facilitate generating an image data.

2. The PET-MR dual modality nuclear medicine imaging system of claim 1, further comprising one or more filters that are coupled to the respective one or more baseline calculation devices, wherein each filter smoothes the digital signals from the respective ADCs by reducing an average peak to peak noise.

3. The PET-MR dual modality nuclear medicine imaging system of claim 1, wherein the one or more baseline calculation devices track the baseline of the digital signals from the respective ADCs for fast changes in the baseline, wherein the fast changes mean a rate of changes greater than 3 ADC least significant bit per micro second, wherein the fast changes occur when the MRI gradient coil is being driven, wherein the one or more baseline calculation devices perform the following for the fast changes:
  determining a second difference between the predetermined value and the first value of the baseline;
  responsive to determining that the second difference exceeds a second predetermined threshold, calculating multiple values of the baseline of the digital signals based on the multiple succeeding samples of the analog electrical signals from the respective ADC;
  calculating differences between the multiple values of the baseline and the predetermined value; and
  responsive to determining that the differences between the multiple values of the baseline and the predetermined value exceed the second predetermined threshold, adjusting the baseline of the digital signals based on at least one of the multiple values of the baseline associated with at least one of the multiple succeeding samples of the analog electrical signals.

4. The PET-MR dual modality nuclear medicine imaging system of claim 3, wherein the one or more baseline calculation devices adjust the baseline for the digital signals based on the differences between the multiple values of the baseline and the predetermined value exceeding the second predetermined threshold in the same direction for several succeeding samples of the analog electrical signals from the respective ADCs.

5. The PET-MR dual modality nuclear medicine imaging system of claim 3, wherein the one or more baseline calculation devices adjust the baseline for the digital signals based on the differences between the multiple values of the baseline from multiple successive succeeding samples and the predetermined value exceeding the second predetermined threshold.

6. The PET-MR dual modality nuclear medicine imaging system of claim 3, wherein the one or more baseline calculation devices adjust the baseline using the latest succeeding sample of the analog electrical signals from the respective ADCs.

7. A method for determining a zero baseline value of a channel from a detector device of a nuclear medicine imagining system to allow for correction of noise or interference on the detector device, comprising:
  calculating a first value of a baseline based on a first sample of analog electrical signals from analog-to-digital converters (ADCs) coupled to the detector device;
  comparing a predetermined value with the first value of the baseline;
  determining a first difference between the predetermined value and the first value of the baseline; and
  responsive to determining that the first difference is less than a first predetermined threshold, adjusting the baseline of the ADCs by a fraction of the difference.

8. The method of claim 7, further comprising:
  determining a second difference between the predetermined value and the first value of the baseline;
  responsive to determining that the second difference exceeds a second predetermined threshold, calculating multiple values of the baseline of the digital signals based on the multiple succeeding samples of the analog electrical signals from the respective ADC,
  calculating differences between the multiple values of the baseline and the predetermined value; and
  responsive to determining that the differences between the multiple values of the baseline and the predetermined value exceed the second predetermined threshold, adjusting the baseline of the ADCs based on at least one of the multiple values of the baseline associated with at least one of the multiple succeeding samples of the analog electrical signals.

9. The method of claim 8, further comprising adjusting the baseline for the digital signals based on the differences between the multiple values of the baseline and the predetermined value exceeding the second predetermined threshold in the same direction for several succeeding samples of the analog electrical signals from the respective ADCs.

10. The method of claim 8, further comprising adjusting the baseline for the digital signals based on the differences between the multiple values of the baseline from multiple successive succeeding samples and the predetermined value exceed the second predetermined threshold.

11. The method of claim 8, further comprising adjusting the baseline for the digital signals using the latest succeeding sample of the analog electrical signals from the respective ADCs.

12. A PET-MR dual modality nuclear medicine imaging system comprising:
  an MRI gradient coil;
  one or more detectors that receive gamma photons;
  one or more analog-to-digital converters (ADCs) that are coupled to the one or more detectors, wherein the one or more ADCs receive analog electrical signals from the one or more detectors corresponding to the received gamma photons and convert the analog electrical signals to digital signals by sampling the analog electrical signals;
  one or more baseline calculation devices for determining a zero baseline value of a channel from the one or more detectors to allow for correction of noise or interference on the detectors, the one or more baseline calculation devices configured to receive the samples of the analog electrical signals from the respective one or more ADCs, wherein each baseline calculation device tracks a baseline of the digital signals from the respective ADCs for slow changes and fast changes in the baseline, wherein the slow changes mean a rate of change less than or equal to 3 ADC least significant bit per micro second, wherein the slow changes occur when the MRI gradient coil is not being driven, wherein the fast changes mean a rate of changes greater than 3 ADC least significant bit per micro second, and wherein the fast changes occur when the MRI gradient coil is being driven,
  wherein for slow changes, the one or more baseline calculation devices perform the following:
    calculate a first value of the baseline based on a first sample of the analog electrical signals from the respective ADCs;
    compare a predetermined value with the first value of the baseline;
    determining a difference between the predetermined value and the first value of the baseline; and
    responsive to determining that the difference is less than a first predetermined threshold, adjusting the baseline of the digital signals by a fraction of the difference,
  wherein for fast changes in the baseline, the one or more baseline calculation devices perform the following:
    determining a second difference between the predetermined value and the first value of the baseline;
    responsive to determining that the second difference exceeds a second predetermined threshold, calculating multiple values of the baseline of the digital signals based on the multiple succeeding samples of the analog electrical signals from the respective ADC;

calculating differences between the multiple values of the baseline and the predetermined value;

responsive to determining that the differences between the multiple values of the baseline and the predetermined value exceed the second predetermined threshold, adjusting the baseline of the digital signals based on at least one of the multiple values of the baseline associated with at least one of the multiple succeeding samples of the analog electrical signals; and a processing device that receives and processes the digital signals based on the adjusted baseline to facilitate generating an image data.

13. The PET-MR dual modality nuclear medicine imaging system of claim 12, wherein the one or more baseline calculation devices adjust the baseline for the digital signals based on the differences between the multiple values of the baseline and the predetermined value exceeding the second predetermined threshold in the same direction for several succeeding samples of the analog electrical signals from the respective ADCs.

14. The PET-MR dual modality nuclear medicine imaging system of claim 12, wherein the one or more baseline calculation devices adjust the baseline for the digital signals based on the differences between the multiple values of the baseline from multiple successive succeeding samples and the predetermined value exceeding the second predetermined threshold.

15. The PET-MR dual modality nuclear medicine imaging system of claim 12, wherein the one or more baseline calculation devices adjust the baseline for the digital signals using the latest succeeding sample of the analog electrical signals from the respective ADCs.

\* \* \* \* \*